United States Patent
Woldike et al.

[11] Patent Number: 5,945,328
[45] Date of Patent: Aug. 31, 1999

[54] PROCESS FOR PRODUCING TRYPSIN (TRYPSINOGEN)

[75] Inventors: Helle Fabricius Woldike; Thomas Borglum Kjeldsen, both of Bagsvaerd, Denmark

[73] Assignee: Novo Nordisk A/S, Bagsvaerd, Denmark

[21] Appl. No.: 08/956,267

[22] Filed: Oct. 22, 1997

Related U.S. Application Data

[63] Continuation of application No. PCT/DK96/00253, Jun. 10, 1996.

[30] Foreign Application Priority Data

Jun. 16, 1995 [DK] Denmark .................................. 0693/95

[51] Int. Cl.⁶ .............................. C12N 1/15; C12N 9/76; C12N 15/55; C12N 15/80
[52] U.S. Cl. ................. 435/213; 435/254.11; 435/254.3; 435/320.1; 536/23.2
[58] Field of Search .................................. 435/69.8, 69.9, 435/476, 483, 213, 254.11, 254.3; 536/23.2

[56] References Cited

U.S. PATENT DOCUMENTS 5,536,661  7/1996  Boel ..................... 435/254.3
5,679,543  10/1997  Lawlis ..................... 435/69.1

FOREIGN PATENT DOCUMENTS 0 597 681    5/1994   European Pat. Off. .
63-160582    7/1988   Japan .
WO94/25583  11/1994   WIPO .
WO 95/15391  6/1995   WIPO .

OTHER PUBLICATIONS

Emi, M. et al. *Gene* 41:305–310 (1986).

Rypniewski, W.R. *Protein Engineering* 7(1):57–64 (1994).

*Primary Examiner*—Dian C. Jacobson
*Attorney, Agent, or Firm*—Steve T. Zelson, Esq.; Reza Green, Esq.

[57] ABSTRACT

Trypsin (trypsinogen) may be produced in a filamentous fungus by transforming a filamentous fungus with a vector comprising a DNA sequence encoding protrypsin or a derivative thereof N-terminally fused to a DNA sequence encoding a signal peptide, culturing the transformed filamentous fungus in a suitable culture medium to produce trypsinogen and recovering trypsinogen and/or trypsin from the medium.

16 Claims, 3 Drawing Sheets

PROCESS FOR PRODUCING TRYPSIN (TRYPSINOGEN)

CROSS-REFERENCE TO RELATED APPLICATIONS

This application is a continuation of Ser. No. PCT/DK96/00253 filed Jun. 10, 1996 and claims priority under 35 U.S.C. 119 of Danish application serial no. 0693/95 filed Jun. 16, 1995, the contents of which are fully incorporated herein by reference.

FIELD OF THE INVENTION

The present invention relates to a process for the production of trypsins in filamentous fungi and to DNA sequences to be used in such processes.

BACKGROUND OF THE INVENTION

In recent years, procedures have been developed for the transformation of filamentous fungi, including *Aspergillus niger*, *Aspergillus oryzae*, and *Aspergillus nidulans*. U.S. Pat. No. 4,885,249 (Allelix) describes a general process for the transformation of *A. niger*, exemplified by the introduction of plasmids carrying genes encoding selectable markers.

This method is generally used for the expression and production of proteins originating from other microbial sources, but mammalian proteins have also been produced in such systems.

However, it has been experienced that the expression of trypsins, especially mammalian trypsins only is accomplished to extremely low levels.

SUMMARY OF THE INVENTION

It has surprisingly been found that when the genes encoding selected trypsinogens (protrypsins) are expressed in *Aspergillus sp.* the levels of trypsin secreted are increased several fold compared to those apparent from other microbial systems.

Accordingly, the present invention relates to a process for the production of trypsins (trypsinogens) or derivatives thereof in filamentous fungi, the process comprising (a) transforming a filamentous fungus host organism with a recombinant DNA vector which comprises a DNA sequence encoding trypsinogen (protrypsin) or a derivative thereof N-terminally fused to a DNA sequence encoding a signal peptide that may be the native sequence or another signal sequence derived from a fungus, such as the *Aspergillus oryzae* TAKA amylase gene or a derivative of such a signal peptide, (b) culturing the transformed filamentous fungus host organism in a suitable culture medium under conditions conducive to the expression of trypsinogen (protrypsin) and secretion of the trypsinogen and trypsin to the medium, and (c) recovering the protrypsin or trypsin or derivative thereof from the medium. In the present context, the term "derivative" is intended to indicate a polypeptide which is derived from the native trypsin or signal peptide (as the case may be) by suitably modifying the DNA sequence coding for the native trypsin/signal peptide, resulting in the addition of one or more amino acid at either or both the C- or N-terminal end, substitution of one or more amino acids at one or a number of different sites in the native amino acid sequence, deletion of one or more amino acids at either or both ends of the native amino acid sequence or at one or more sites within the native sequence, or insertion of one or more amino acids at one or more sites in the native amino acid sequence. Such modifications of the DNA sequence may be done by methods well known in the art.

The term "filamentous fungus" is intended to include the groups Phycomycetes, Zygomycetes, Ascomycetes, Basidiomycetes and fungi imperfecti, including Hyphomycetes such as the genera Aspergillus, Penicillium, Trichoderma, Fusarium and Humicola.

The presence of the signal sequence serves to direct the expressed trypsinogen or derivative thereof effectively into the secretory pathway of the host cell so that trypsinogen or trypsin may readily be isolated from the culture medium (at least some of the product recovered will be mature trypsin as the trypsinogen secreted from the cells is either subjected to automaturation or maturation by proteases produced by the host cell).

In the present invention the signal sequence does not seem to be critical, and a number have been tested, such as the TAKA-amylase (ref. EP 0 238 023), the PTRYP-trypsin, and the human HTRYPI-trypsin and HTRYPII signal sequences (Okayama et al., *Methods in Enzymology* 154, 3–28 (1987), Emi et al., *Gene* 41, 305–310, (1986)).

The trypsin (trypsinogen) to be produced by the process of the invention is trypsin of any origin, especially mammalian trypsin, such as porcine, bovine, and human trypsin.

The invention furthermore comprises certain DNA sequences coding for porcine trypsin (trypsinogen) and alleles thereof capable of expressing trypsins having retained their biological activity.

Furthermore the invention relates to vectors comprising said DNA sequence and hosts transformed therewith.

BRIEF DESCRIPTION OF THE TABLES AND DRAWING

The invention is described in further detail in the following parts of the specification with reference to the Examples and the drawing, wherein FIG. 1 shows the steps involved in the construction of pHW470, FIG. 2 shows the steps involved in the construction of pHW473, and FIG. 3 shows the steps involved in the construction of pHW874.

DETAILED DESCRIPTION OF THE INVENTION

Figure 1:
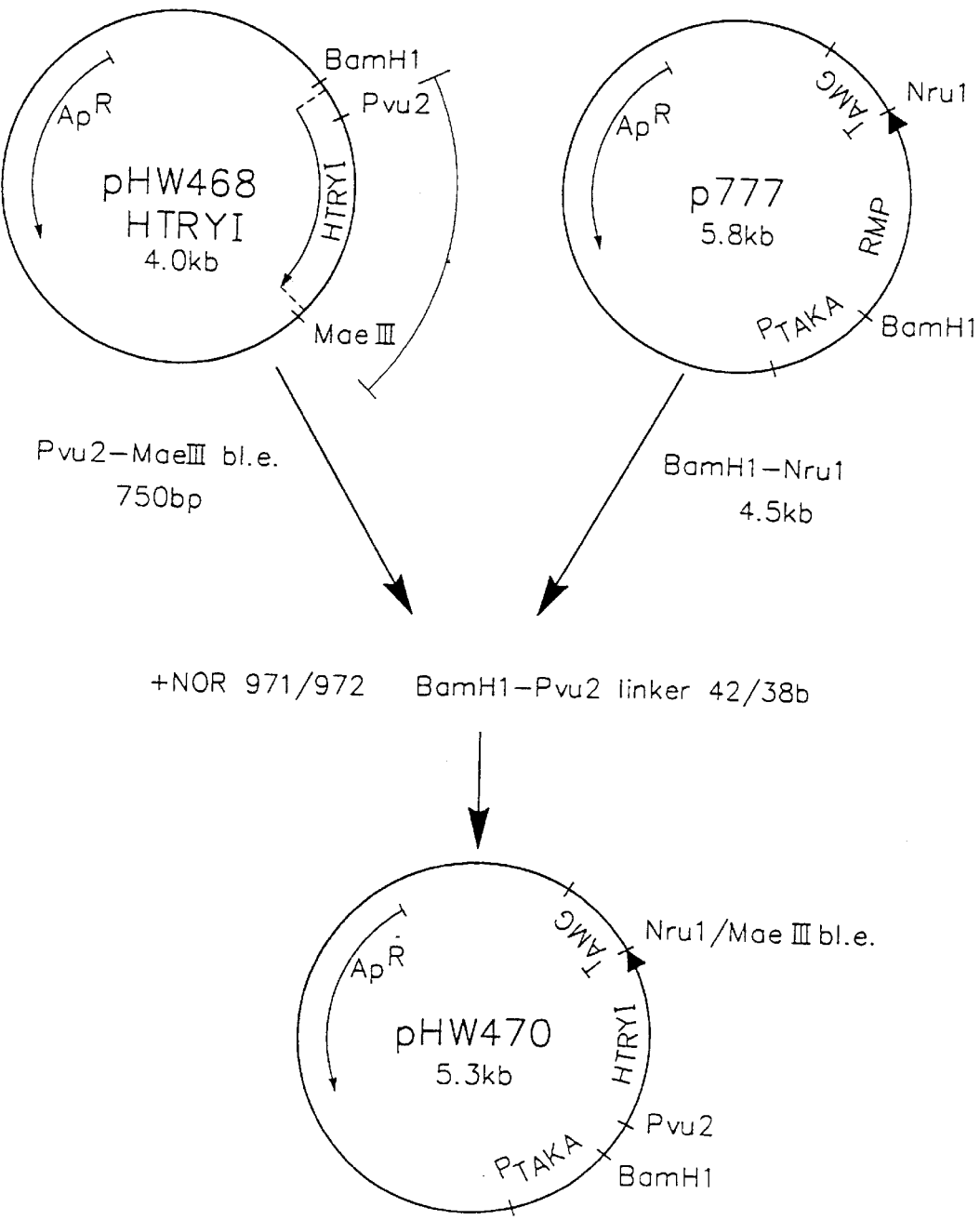

As indicated the present invention in its first aspect relates to a process for the production of trypsins (trypsinogens) or derivatives thereof in filamentous fungi, the process comprising:

(a) transforming a filamentous fungus host organism with a recombinant DNA vector which comprises a DNA sequence encoding trypsinogen or a derivative thereof N-terminally fused to a DNA sequence encoding a signal peptide that may be the native sequence or another signal sequence derived from a fungus, such as the *Aspergillus oryzae* TAKA amylase gene or a derivative of such a signal peptide, (b) culturing the transformed filamentous fungus host organism in a suitable culture medium under conditions conducive to the expression of protrypsin and secretion thereof to the medium, and (c) recovering the trypsinogen or trypsin or derivative thereof from the medium.

The vector may further comprise DNA sequences encoding functions facilitating gene expression, typically a promoter, transcription initiation sites, and transcription termination and polyadenylation functions.

The promoter which may be preceded by upstream activating sequences and enhancer sequences as known in the art may be any DNA sequence exhibiting a strong transcriptional activity in *Aspergillus sp.*, such as *A. oryzae* and *A. niger*, and may be derived from a gene encoding an extracellular or intracellular protein such as an amylase, a glucoamylase, a protease, a lipase, a cellulase or a glycolytic enzyme.

Examples of suitable promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, or *A. oryzae* alkaline protease. Examples of promoters from genes encoding glycolytic enzymes are the *A. oryzae* triose phosphate isomerase, ADH and PGK promoters.

The filamentous fungus used as the host organism is preferably selected from an *Aspergillus sp.* such as *A. niger, A. awamori* or *A. oryzae*.

Termination and polyadenylation sequences may suitably be derived from the same sources as the promoter.

The techniques used to transform the host organism may suitably be adapted from the methods of transforming *A. nidulans* described in, for instance, Yelton et al., *Proc. Natl. Acad. Sci. USA* 81, 1984, pp. 1470–1474, or EP 0 215 594, from the methods of transforming *A. niger* described in, for instance Buxton et al., *Gene* 37, 1985, pp. 207–215 or U.S. Pat. No. 4,885,249, or from the methods of transforming *A. oryzae* described in EP 238023. In the process of the present invention, *A. oryzae* or *A. niger* may be transformed with a vector system comprising a DNA sequence coding for a selection marker which is capable of being incorporated in the genome of the host organism on transformation, but which is either not expressed by the host before transformation or not expressed in sufficient amounts to permit growth under selective conditions. Transformants can then be selected and isolated from non-transformants on the basis of the incorporated selection marker.

Suitable selection markers may be derived from the *A. nidulans* or *A. niger* argB gene, the *A. nidulans* trpC gene, the *A. nidulans* amdS gene, the *Neurospora crassa* pyr4 or DHFR genes, or the *A. niger* or *A. oryzae* niaD gene.

Preferred selection markers for use in the present invention are derived from the *A. nidulans* or *A. niger* amdS or argB genes. If argB is chosen as the selection marker, an ArgB– mutant strain (which does not express the ArgB gene) must be used as the host organism. On the other hand, the amdS gene may be used as the selection marker in wild-type *A. oryzae* or *A. niger* strains which do not express this gene in sufficient amounts to permit growth under selective conditions.

The signal sequence may be chosen from signal sequences derived from the trypsinogen gene itself, or from a gene encoding e.g. *A. oryzae* TAKA amylase, *Rhizomucor miehei* aspartic proteinase, *A. niger* neutral α-amylase, *A. niger* acid stable a-amylase, *A. niger* glucoamylase, *Rhizomucor miehei* lipase, or *A. oryzae* alkaline protease. Examples of genes encoding glycolytic enzymes are the *A. oryzae* triose phosphate isomerase, ADH and PGK. Combinations and/or variants of such signal sequences may also be used.

The gene coding for trypsinogen fused to the signal sequence as well as to promoter and terminator sequences may be inserted in a vector containing the selection marker, or it may be inserted in a separate vector for introduction into the host cell. The vector or vectors may be linear or closed circular molecules.

The medium used to culture the transformed host cells may be any conventional medium suitable for growing filamentous fungi. The transformants are usually stable and may be cultured in the absence of selection pressure. However, if the transformants are found to be unstable, the selection marker introduced into the cells may be used for selection.

The trypsinogen or trypsin produced by the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

The invention furthermore comprises certain DNA sequences coding for porcine trypsin (trypsinogen) and alleles thereof capable of expressing trypsins having retained their biological activity.

The invention relates in a further aspect to vectors comprising said DNA sequences.

The invention also encompasses hosts transformed with such vectors. The hosts may be of animal or microbial origin, such as mammalian cell lines, bacteria, yeasts or fungi, especially filamentous fungi.

Finally the invention relates to a method of recombinantly producing porcine trypsin, the process comprising (a) transforming a host with a recombinant DNA vector which comprises a DNA sequence encoding porcine trypsinogen or a derivative thereof N-terminally fused to a DNA sequence encoding a signal peptide that may be the native sequence or another signal sequence or a derivative of such a signal peptide, (b) culturing the transformed host in a suitable culture medium under conditions conducive to the expression of porcine trypsinogen and secretion thereof to the medium, and (c) recovering the porcine trypsinogen or trypsin or derivative thereof from the medium.

The invention is further illustrated in the following examples which are not in any way to be construed as limiting to the scope of the invention as claimed.

MATERIALS AND METHODS

EXAMPLES

Example 1

Cloning of Human Trypsinogen I and II cDNA

From a human pancreatic cDNA library constructed according to Okayama et al., Methods in Enzymology 154. 3–28 (1987), we isolated cDNA clones encoding the two major human trypsinogen isozymes, TRYI and TRYII. The sequences of Emi et al., Gene 41, 305–310, (1986), were used to select probes for isolation:

```
                                              SEQ ID NO: 3
NOR 948: 5' GCCCCCAACGATCTTGTCATCATCATC 3'

SEQ ID NO: 4
NOR 948: 5' GTTCAGAGTCTTCCTGTCGTATTGGGG 3'
```

NOR 948 is common to TRYI and TRYII, NOR 949 is specific for TRYII. Full length clones were isolated having sequences in accordance with the ones published by Emi et al., Gene 41, 305–310 (1986). The plasmids were designated pHW468 for TRYI and pHW469 for TRYII.

Example 2.
Cloning of Porcine Trypsinogen cDNA.

mRNA was purified from porcine pancreas using standard methods (Maniatis 1982). cDNA was prepared from the MRNA, purified and inserted into λgt11 using the cDNA cloning system-λgt11 from Amersham, UK. Preparation of phage, plating cells, infection with λgt11, amplification and screening was performed according to the manufacturers introductions and standard techniques (Maniatis 1982). The oligonucleotide NOR 948, as described above, was used for screening of plaques.

Positive plaques were isolated and amplified. The isolated λgt11 DNA was subjected to digestion with EcoR1 and the inserted cDNA was cloned into EcoR1 cleaved pBluescript SK (Stratagene) using ampicillin selection of *E. coli* JM101 transformants. The selected plasmid was shown by DNA sequencing analysis (Sequenase, U.S. Biochemical Corp.) to contain a cDNA sequence compatible with the known porcine trypsin amino acid sequence (Hermodson et al., Biochemistry 12, 3146–3153 (1973)). The almost complete sequence lacking the very N-terminal end of the signal peptide of porcine pre-pro-trypsin was obtained from 2 EcoR1 fragments of 130 bp covering the N-terminal and 740 bp covering the C-terminal The resulting plasmid was designated p185, the sequence of which is shown in SEQ ID NO: 1.

Example 3
Expression of Human Trypsinogen I and II in *A. oryzae*.

Figure 2:
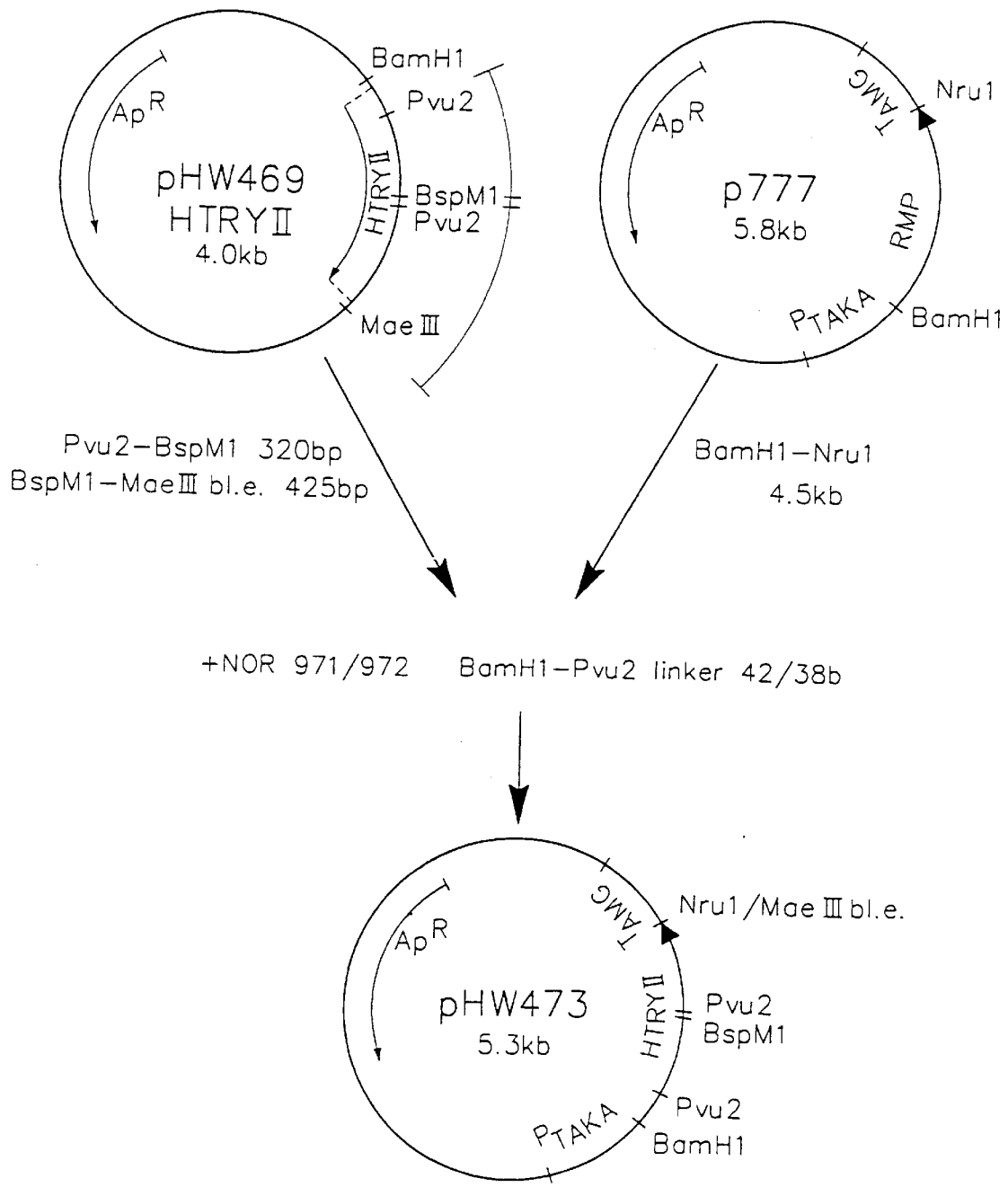

Vectors for expression of human trypsinogen I and II in Aspergillus were constructed as outlined in FIG. 1 and FIG. 2. The BamH1-PvuII linker:

```
NOR 971: 5' GATCCACCATGAATCCACTCCTGATCCTTACCTTTGTGGCAG 3'

NOR 972: 3'     GTGGTACTTAGGTGAGGACTAGGAATGGAAACACCGTC 5'

SEQ ID NO: 5
``` connects the cDNA to the BamH1 site in the fungal expression vector p777 described in EP 0 238 023. The common linker covers the first 11 amino acids of the signal sequence of TRYI, differing only in position 3 from TRYII, which has a leucine instead of proline in its native sequence. The remaining part of the sequence is native to both species.

The trypsinogen expression vectors pHW470 and pHW473 were transformed into *A. oryzae* IFO 4177, or a protease deficient derivative thereof, A1560-T40, using the procedure described in EP 238023. Selection on acetamide was performed by co-transformation with pToC 186 as described in WO 93/00426.

Transformants were grown in YPD medium (Sherman et al.,Methods in Yeast Genetics, Cold Spring Harbor Laboratory, 1981) for 3–4 days and analysed for new protein species in the supernatant by SDS-PAGE and Western blot, using polyclonal antibody raised against porcine trypsin, which did not appear to detect the human trypsin species. However, activity assays using L-BAPNA (L-Benzoyl-arginyl-paranitro anilide) as substrate demonstrated convincingly the expression of TRYI and TRYII from *A. oryzae*. Also, both species were purified from *A. oryzae* supernatants.

Example 4
Expression of Porcine Trypsin in *A. oryzae*

Figure 3:
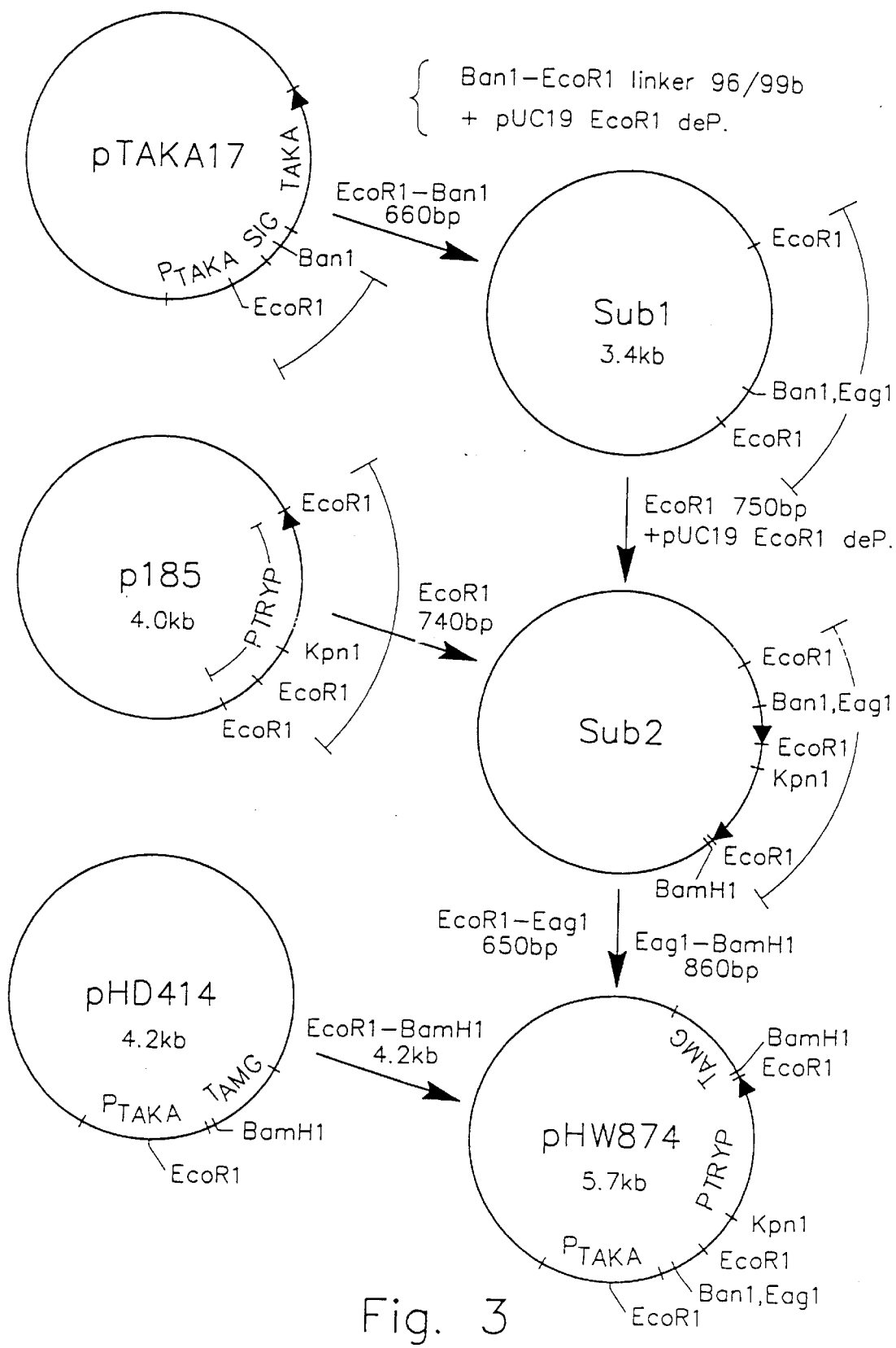

A vector for expression of porcine trypsinogen in Aspergillus was constructed as outlined in FIG. 3. To connect the first 18 amino acids of the TAKA amylase signal to the last 4 amino acids of the porcine trypsin signal, we used a Ban1-EcoR1 linker:

```
226/223:
5' GCACCGGCCGCGGTGGCCTTCCCGACCGACGATGACGACAAGATCGTCGGCGG

3'     GCCGGCGCCACCGGAAGGGCTGGCTGCTACTGCTGTTCTAGCAGCCGCCC

225/224:
TACACGTGTGCAGCGAACTCGATCCCTTACCAGGTCTCGCTG          3' 96b

ATGTGCACACGTCGCTTGAGCTAGGGAATGGTCCAGAGCGACTTAA 5'    99b

SEQ ID NO: 6
```

This fusion also has a part of the TAKA amylase promoter and the N-terminal end of the trypsin gene. The C-terminal region of the trypsin gene is joined to this in Sub2, keeping track of the orientations. The final expression vector, pHW874, has TAKA amylase promoter and AMG terminator as functional elements. These elements were derived from pHD414, which is described in EP 0 505 311.

The porcine trypsin expression vector pHW874 was transformed into *A. oryzae* as described in Example 3. Transformants were grown in YPD medium and analysed by SDS-PAGE-Western and by cleavage of L-BAPNA, as described in Example 3. In this case distinct bands of the expected size for porcine trypsinogen and mature trypsin were seen on Western blots, corresponding to activity measurements with L-BAPNA.

REFERENCES CITED IN THE SPECIFICATION

U.S. Pat. No. 4,885,249 (Allelix)
Okayama et al., *Methods in Enzymology* 154, 3–28 (1987)
Emi et al., *Gene* 41, 305–310, (1986)
Yelton et al., *Proc. Natl. Acad. Sci. USA* 81, 1984, pp. 1470–1474
EP 0 215 594
Buxton et al., *Gene* 37, 1985, pp. 207–215
U.S. Pat. No. 4,885,249
EP 0 238 023
Hermodson et al., Biochemistry 12, 3146–3153 (1973)
WO 93/00426.
Sherman et al., Methods in Yeast Genetics, Cold Spring Harbor Laboratory, 1981
EP 0 505 311

What is claimed:

1. A process for the production of mammalian trypsinogen or trypsin in a filamentous fungus, the process comprising
    (a) transforming a filamentous fungus host organism with a recombinant DNA vector which comprises a DNA sequence encoding trypsinogen N-terminally fused to a DNA sequence encoding a signal peptide,
    (b) culturing the transformed filamentous fungus host organism in a suitable culture medium under conditions conducive to the expression of trypsinogen and secretion thereof to the medium, and
    (c) recovering the expressed trypsinogen or trypsin thereof from the medium.

2. The process of claim 1, wherein the filamentous fungus is an *Aspergillus sp.*

3. The process of claim 2, wherein the *Aspergillus sp.* is *A. niger* or *A. oryzae*.

4. The process of claim 3, wherein the DNA vector further comprises a promoter selected from the group consisting of an *A. niger* amylase promoter and an *A. oryzae* TAKA amylase promoter.

5. The process of claim 1, wherein said signal sequence is selected from the group consisting of a native trypsinogen signal sequence, an *A. niger* amylase signal sequence, and an *A. oryzae* TAKA amylase signal sequence.

6. The process of claim 1, wherein said mammalian trypsin or trypsinogen is derived from a human or a pig.

7. An isolated DNA encoding a porcine trypsinogen having the amino acid sequence of SEQ ID NO: 2.

8. A vector comprising a DNA sequence of claim 7.

9. A host cell transformed with a vector of claim 8.

10. The host cell of claim 9, which is a mammalian host.

11. The host cell of claim 9, which is a microbial host.

12. The host of claim 11, which is a yeast or fungus.

13. The host of claim 12, which is a filamentous fungus.

14. A method of recombinantly producing porcine trypsinogen or trypsin, the process comprising
    (a) transforming a host cell with a recombinant DNA vector which comprises a DNA sequence encoding porcine trypsinogen N-terminally fused to a DNA sequence encoding a signal peptide, wherein said signal peptide is selected from the group consisting of the native porcine trypsinogen signal sequence and a heterologous signal sequence, (b) culturing the transformed host in a suitable culture medium under conditions conducive to the expression of porcine trypsinogen and secretion thereof to the medium, and (c) recovering the porcine trypsinogen or trypsin or derivative thereof from the medium.

15. An isolated DNA encoding porcine trypsinogen, wherein the amino acid sequence of said porcine trypsinogen comprising the amino acid sequence of SEQ ID NO: 2.

16. An isolated DNA encoding porcine trypsinogen comprising the nucleotide sequence of SEQ ID NO: 1.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 897 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION:4..744

(xi) SEQUENCE DESCRIPTION: SEQ ID NO: 1:

```
GGA ATT CCG AAC ACC TTT GTC TTG CTT GCG CTC CTG GGA GCT GCT GTT        48
    Ile Pro Asn Thr Phe Val Leu Leu Ala Leu Leu Gly Ala Ala Val
     1               5                  10                  15

GCT TTC CCC ACG GAT GAT GAT GAC AAG ATC GTC GGG GGT TAC ACC TGT        96
Ala Phe Pro Thr Asp Asp Asp Asp Lys Ile Val Gly Gly Tyr Thr Cys
                 20                  25                  30

GCA GCA AAT TCC ATT CCC TAC CAG GTG TCC CTG AAT TCT GGC TCC CAC       144
Ala Ala Asn Ser Ile Pro Tyr Gln Val Ser Leu Asn Ser Gly Ser His
             35                  40                  45

TTC TGT GGT GGG TCC CTC ATC AAC AGC CAG TGG GTG GTG TCT GCT GCT       192
Phe Cys Gly Gly Ser Leu Ile Asn Ser Gln Trp Val Val Ser Ala Ala
         50                  55                  60

CAC TGC TAC AAG TCC CGA ATC CAG GTG CGT CTG GGA GAA CAC AAC ATC       240
His Cys Tyr Lys Ser Arg Ile Gln Val Arg Leu Gly Glu His Asn Ile
     65                  70                  75

GAC GTC CTT GAG GGC AAT GAG CAA TTC ATC AAT GCC GCC AAG ATC ATC       288
Asp Val Leu Glu Gly Asn Glu Gln Phe Ile Asn Ala Ala Lys Ile Ile
 80                  85                  90                  95

ACC CAC CCC AAT TTC AAT GGA AAT ACC TTA GAT AAC GAC ATC ATG CTG       336
Thr His Pro Asn Phe Asn Gly Asn Thr Leu Asp Asn Asp Ile Met Leu
                100                 105                 110

ATT AAA CTG AGC TCA CCT GCC ACT CTC AAC AGT CGA GTA GCA ACT GTC       384
Ile Lys Leu Ser Ser Pro Ala Thr Leu Asn Ser Arg Val Ala Thr Val
            115                 120                 125

TCA CTG CCA AGA TCT TGT GCA GCT GCT GGT ACC GAG TGT CTC ATC TCT       432
Ser Leu Pro Arg Ser Cys Ala Ala Ala Gly Thr Glu Cys Leu Ile Ser
        130                 135                 140

GGC TGG GGC AAC ACC AAA AGC AGT GGC TCC AGC TAC CCT TCG CTC CTG       480
Gly Trp Gly Asn Thr Lys Ser Ser Gly Ser Ser Tyr Pro Ser Leu Leu
    145                 150                 155

CAA TGC CTG AAG GCC CCC GTC CTA AGT GAC AGT TCT TGC AAG AGT TCC       528
Gln Cys Leu Lys Ala Pro Val Leu Ser Asp Ser Ser Cys Lys Ser Ser
160                 165                 170                 175

TAC CCA GGC CAG ATC ACC GGA AAC ATG ATC TGT GTC GGC TTC CTG GAG       576
Tyr Pro Gly Gln Ile Thr Gly Asn Met Ile Cys Val Gly Phe Leu Glu
                180                 185                 190

GGT GGT AAG GAT TCT TGC CAG GGA GAC TCT GGT GGC CCC GTG GTC TGC       624
Gly Gly Lys Asp Ser Cys Gln Gly Asp Ser Gly Gly Pro Val Val Cys
            195                 200                 205

AAT GGA CAG CTC CAG GGT ATT GTC TCT TGG GGC TAT GGC TGC GCC CAG       672
Asn Gly Gln Leu Gln Gly Ile Val Ser Trp Gly Tyr Gly Cys Ala Gln
        210                 215                 220
```

```
AAA AAC AAG CCT GGG GTC TAC ACC AAG GTC TGC AAC TAT GTG AAC TGG      720
Lys Asn Lys Pro Gly Val Tyr Thr Lys Val Cys Asn Tyr Val Asn Trp
            225                 230                 235

ATT CAG CAG ACC ATC GCT GCC AAC TAAAGAATTT CATTTCTTCA TGACTCTTCC     774
Ile Gln Gln Thr Ile Ala Ala Asn
240                 245

CTTTAGTCAT CTTCACCTTC CTCCCATCCT GCGAACAGCA TCTAAATAAA AACATTTTGA    834

CCTGTACCAG CATCTAAATA AAAACATTTT GAGCTGTACC CAAAAAAAAA AAAAAGGAAT    894

TCC                                                                 897

(2) INFORMATION FOR SEQ ID NO: 2:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO: 2:

Ile Pro Asn Thr Phe Val Leu Leu Ala Leu Leu Gly Ala Ala Val Ala
1               5                   10                  15

Phe Pro Thr Asp Asp Asp Asp Lys Ile Val Gly Gly Tyr Thr Cys Ala
                20                  25                  30

Ala Asn Ser Ile Pro Tyr Gln Val Ser Leu Asn Ser Gly Ser His Phe
            35                  40                  45

Cys Gly Gly Ser Leu Ile Asn Ser Gln Trp Val Ser Ala Ala His
        50                  55                  60

Cys Tyr Lys Ser Arg Ile Gln Val Arg Leu Gly Glu His Asn Ile Asp
65                  70                  75                  80

Val Leu Glu Gly Asn Glu Gln Phe Ile Asn Ala Ala Lys Ile Ile Thr
                85                  90                  95

His Pro Asn Phe Asn Gly Asn Thr Leu Asp Asn Asp Ile Met Leu Ile
                100                 105                 110

Lys Leu Ser Ser Pro Ala Thr Leu Asn Ser Arg Val Ala Thr Val Ser
            115                 120                 125

Leu Pro Arg Ser Cys Ala Ala Ala Gly Thr Glu Cys Leu Ile Ser Gly
130                 135                 140

Trp Gly Asn Thr Lys Ser Ser Gly Ser Ser Tyr Pro Ser Leu Leu Gln
145                 150                 155                 160

Cys Leu Lys Ala Pro Val Leu Ser Asp Ser Ser Cys Lys Ser Ser Tyr
                165                 170                 175

Pro Gly Gln Ile Thr Gly Asn Met Ile Cys Val Gly Phe Leu Glu Gly
            180                 185                 190

Gly Lys Asp Ser Cys Gln Gly Asp Ser Gly Gly Pro Val Val Cys Asn
        195                 200                 205

Gly Gln Leu Gln Gly Ile Val Ser Trp Gly Tyr Gly Cys Ala Gln Lys
210                 215                 220

Asn Lys Pro Gly Val Tyr Thr Lys Val Cys Asn Tyr Val Asn Trp Ile
225                 230                 235                 240

Gln Gln Thr Ile Ala Ala Asn
                245

(2) INFORMATION FOR SEQ ID NO: 3:

(i) SEQUENCE CHARACTERISTICS:
        (A) LENGTH: 27 base pairs
        (B) TYPE: nucleic acid
```

```
            (C) STRANDEDNESS: single
            (D) TOPOLOGY: linear (xi) SEQUENCE DESCRIPTION: SEQ ID NO: 3:

GCCCCCAACG ATCTTGTCAT CATCATC                                      27

(2) INFORMATION FOR SEQ ID NO: 4:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 4:

GTTCAGAGTC TTCCTGTCGT ATTGGGG                                      27

(2) INFORMATION FOR SEQ ID NO: 5:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO: 5:

GATCCACCAT GAATCCACTC CTGATCCTTA CCTTTGTGGC AG                     42

(2) INFORMATION FOR SEQ ID NO: 6:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (xi) SEQUENCE DESCRIPTION: SEQ ID NO: 6:

GCACCGGCCG CGGTGGCCTT CCCGACCGAC GATGACGACA AGATCGTCGG CGGGTACACG  60

TGTGCAGCGA ACTCGATCCC TTACCAGGTC TCGCTG                            96
```